(12) United States Patent
Schleser et al.

(10) Patent No.: US 7,329,546 B2
(45) Date of Patent: Feb. 12, 2008

(54) METHOD FOR DETERMINING RATIO OF OXYGEN ISOTOPES IN OXYGEN-CONTAINING SOLIDS BY HEATING IN GRAPHITE CRUCIBLE

(75) Inventors: Gerhard Hans Schleser, Mönchengladbach (DE); Wolfgang Knörchen, Aldenhoven (DE)

(73) Assignee: Forschungszentrum Julich GmbH, Julich (DE)

( * ) Notice: Subject to any disclaimer, the term of this patent is extended or adjusted under 35 U.S.C. 154(b) by 596 days.

(21) Appl. No.: 10/886,868

(22) Filed: Jul. 7, 2004

(65) Prior Publication Data

US 2005/0008543 A1 Jan. 13, 2005

Related U.S. Application Data

(62) Division of application No. 09/913,344, filed as application No. PCT/DE00/00425 on Feb. 11, 2000, now abandoned.

(30) Foreign Application Priority Data

Feb. 18, 1999 (DE) ................. 199 06 732

(51) Int. Cl.
*G01N 23/00* (2006.01)
(52) U.S. Cl. ........................................................ 436/58
(58) Field of Classification Search ..................... None
See application file for complete search history.

(56) References Cited

U.S. PATENT DOCUMENTS 4,800,747 A * 1/1989 Tsuji et al. ................ 73/19.07

FOREIGN PATENT DOCUMENTS

| JP | 02298861 A | * | 12/1990 |
| JP | 04104054 A | * | 4/1992 |

* cited by examiner

*Primary Examiner*—Yelena G. Gakh
(74) *Attorney, Agent, or Firm*—Jonathan Myers; Andrew Wilford

(57) ABSTRACT

Oxygen isotropes are labeled from oxygen containing solids by heating the solids in a graphite crucible by induction to produce Co and/or $Co_2$.

7 Claims, 1 Drawing Sheet

ND FOR DETERMINING RATIO OF
METHOD FOR DETERMINING RATIO OF OXYGEN ISOTOPES IN OXYGEN-CONTAINING SOLIDS BY HEATING IN GRAPHITE CRUCIBLE

CROSS REFERENCE TO RELATED APPLICATIONS

This application division of Ser. No. 09/913,344 filed on Aug. 10, 2001 now abandoned which is a national phase of PCT/DE 00/00 425 filed 11 Feb. 2000 and is based upon a German national application 199 06 732.5 filed 18 Feb. 1999 under the International Convention.

FIELD OF THE INVENTION

The invention relates to a method of liberating oxygen isotopes from oxygen-containing solids, especially from biogenic and nonbiogenic silicate-based substances or solids as well as to a crucible suitable for carrying out the method.

BACKGROUND OF THE INVENTION

In paleoclimatology and paleothermometry there is interest in determining the proportions of the oxygen isotopes $^{16}O$ and $^{18}O$ in solid samples.

From the work "Stable Isotope Geochemistry" of J. Hoefs, $4^{th}$ Completely Revised, Updated and Enlarged edition, Springer, Berlin, Heidelberg, New York, Barcelona, Budapest, Hong Kong 1997, various methods of liberating oxygen from samples are known. Thus silicate-based samples of solids to be investigated are evaporated according to the state of the art, whereby oxygen is liberated and the analysis can proceed therewith. The oxygen can be investigated directly by mass spectroscopy as to its isotopes. Alternatively, the oxygen can be transformed in a further reaction with carbon into CO or $CO_2$. The determination of the isotope ratio is then effected by mass spectroscopic investigation of the CO or $CO_2$ resulting from reaction with graphite.

Another method which has come into use mainly with silicates and oxides is based upon the fluorination of the substances whose oxygen isotopes are to be analyzed. In this case, the oxygen is liberated by means of $F_2$ or $BrF_5$ in nickel cylinders at 500 to 600° C. The oxygen thereafter is generally transformed to $CO_2$ on hot graphite and is then subjected to the mass spectroscopic measurement. Frequently the sample to be investigated requires a prepurification, because foreign molecules or groups which are detrimental to the analysis can be incorporated in the sample. Thus, for example biogenic silicates like the shells of diatoms frequently contain water or OH groups which make an analytic oxygen isotope determination very difficult. Should an analysis of the isotope composition of the oxygen nevertheless have to be carried out, the samples frequently initially must be freed from the foreign substances or molecules by preliminary purification steps which can falsify the analysis result. A method of liberating oxygen from the sample to be tested is the laser vaporization of partial regions of solids. In this method it is not possible to avoid a slight fractionation, which means a shift in the oxygen isotope ratio of the solid sample to be analyzed and which is based upon the somewhat different conditions in the boundary regions of the evaporation process. The heating of the solid sample by laser has therefore significant drawbacks with respect to the representativity or reproducibility of the results with large samples which can be heated only at point-like regions of the entire solid sample by the laser beam and thus makes the isotope analysis accessible. In the case of inhomogeneities in a sample, the results of the respective measurements of the ratios of the oxygen isotopes are not truly representative for the entire sample. To obtain representative results, therefore, many measurements are required whose results must be averaged.

OBJECT OF THE INVENTION

It is therefore the object of the invention to provide a method and a crucible by means of which solid samples, above all biogenic silicates or biogenic silicon dioxide, can be analyzed in a single operation without pretreatment especially to liberate from the sample adhering $H_2O$ molecules or OH groups, and also without the need for averaging the results.

SUMMARY OF THE INVENTION

This object is attained in a method of liberating oxygen isotopes from oxygen-containing solids in which the solids are heated by being brought into contact with graphite and subjected to induction heating whereby CO and/or $CO_2$ result.

With the method according to the invention it is possible directly to obtain results for the ratio of the isotope oxygen composition in solid samples of such problematical materials like biogenic silicates in a sequence collectively forming a single operation. It is therefore no longer necessary to have any special separate experimental steps of the prepreparation of the sample. Consequently, a significant reduction in the work and time requirements is possible. In addition, the method of the invention enables the analysis of the oxygen isotope ratios of samples without having to deal with the inhomogeneities of the sample on the quality of the measurement results with respect to the complete sample. Apart from quantities which are measurable by mass spectroscopy in a problem-free manner, the sample quantities for example for silicate in flow mode can be reduced to 50 µg $SiO_2$ which cannot be as easily handled with chemical decomposition methods. With very heterogeneous samples, however, larger samples of at least 100 µg $SiO_2$ or more are preferred to permit a reliable mean value to be obtained.

According to the invention, the heating up of the solids is effected in vacuum. The CO or $CO_2$ resulting from the heating of the solids can be isolated. The CO or $CO_2$ can be fed to an analysis process which preferably is a mass spectroscopic process. The solid can be a silicate and the heating can be carried out from 1600 to 2200° C. Preferably, the heating is carried out sequentially to drive off impurities like water. An apparatus for liberating oxygen isotopes from oxygen-containing solids can include a graphite crucible and an induction source. The graphite crucible can be provided in a vacuum-tight housing of quartz glass to which a pump is connected. The apparatus can comprise means for capturing gaseous CO or $CO_2$ arising from induction. The housing of quartz glass can be provided with means for cooling it. The housing can be opened on opposite sides to replace the solid with the graphite crucible. The graphite crucible can be elongated whereby at an upper end a cavity is provided for receiving the solids and at the opposite end an axial bore is provided which can receive a rod with which the graphite crucible can be mounted in, the housing.

BRIEF DESCRIPTION OF THE DRAWING

The sole FIGURE of the drawing is a cross sectional view of an apparatus according to the invention.

SPECIFIC DESCRIPTION

Figure 1:
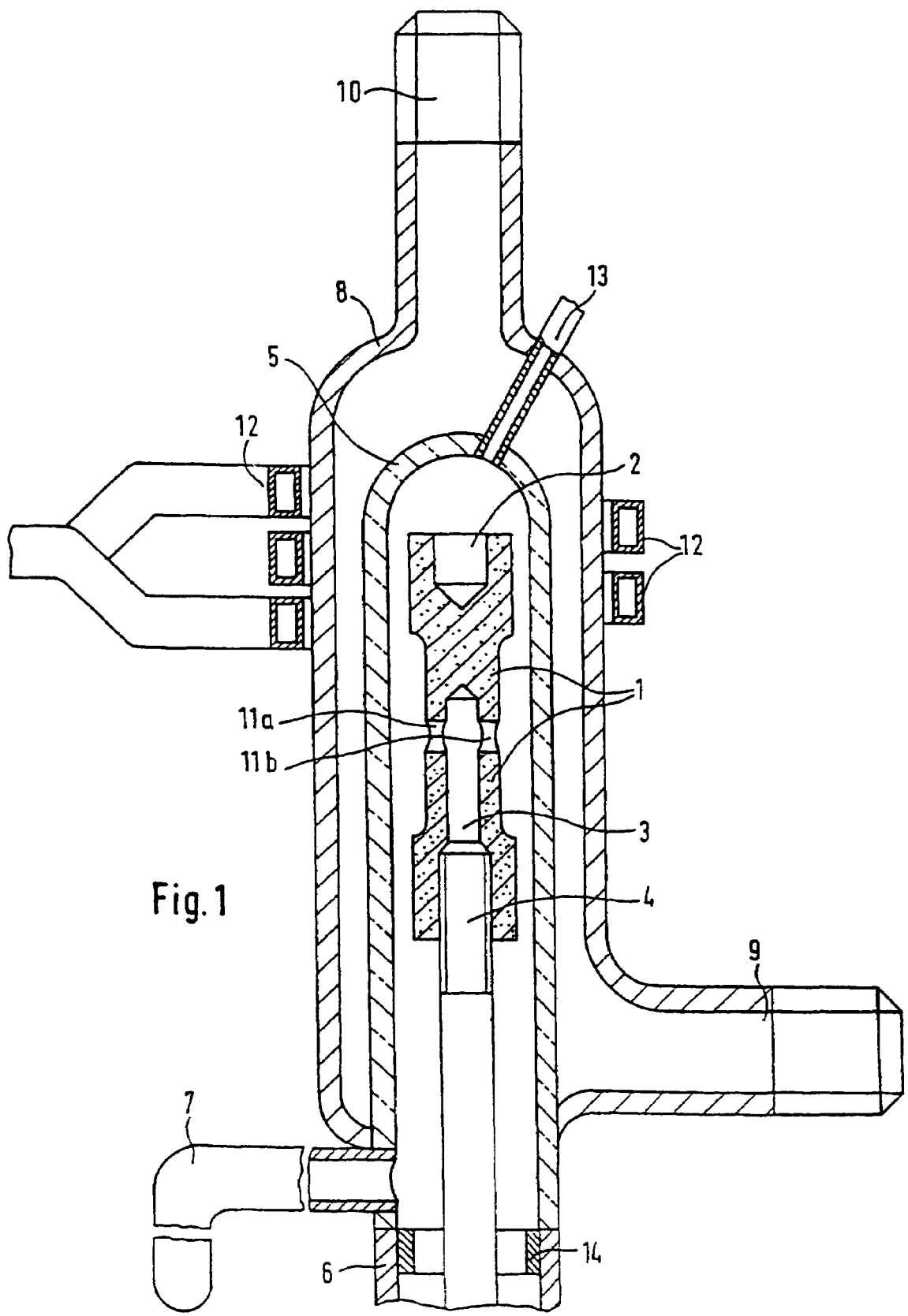

The apparatus according to the invention shown in FIG. 1 comprises a graphite crucible 1 which is elongated, whereby at the upper end a cavity 2 is formed to receive a solid and at the opposite end a bore 3 is provided which receives a rod 4 by means of which the graphite crucible 1 can be mounted in a housing 5 which is comprised of quartz glass.

The housing 5 is connected in a vacuum-tight manner by a connected part 6 to a pump which has not been illustrated in FIG. 1. For special investigation, a cooling finger 7 is integrated in the device and in which water driven thermally out of the sample can be collected.

The housing 5, which contains the graphite crucible 1 is enclosed in a cooling jacket 8 which has a coolant inlet 9 and a coolant outlet 10.

The graphite crucible 1 has bores 11a and 11b which extend radially with respect to the longitudinal axis of the graphite crucible and provide a connection between the bore 3 and the environment around the graphite crucible 1.

The housing 5 is surrounded at the level of the cavity 2 of the graphite crucible 1 by an induction coil 12 which is connected with a medium frequency generator (MF generator).

In the cooling jacket 8, at the outer sides and at the angle of 180°, two helium ducts 13 are integrated through which the carrier gas helium can flow into the housing 5 to serve as a carrier for CO or $CO_2$ which is to be fed to a mass spectrometer. In the connecting part 6 there is to be found a palladium ring 14.

In the operation of the apparatus according to the invention, the graphite crucible 1, together with the solid sample, which in this example is a silicate, together with the rod 4 is introduced into the housing manually or automatically. The pump is connected via an adapter which is connected to the connection part 6. The housing 5 is comprised preferably of quartz glass since this is inert under the experimental conditions and provides no exchange of oxygen atoms at the high temperatures of the quartz glass with the oxygen produced in the experiment. The coolant jacket 8 is traversed by water supplied via the coolant inlet and which is discharged through the coolant outlet 10. The water cooling is effected in a bypass through the MF generator cooling circuit through which, via a further bypass, the induction coil is also cooled.

The induction coil is energized via the MF generator so that the graphite crucible 1 is inductively heated. The heating up time can be selected freely and can be controllable steplessly to 2200° C. The heating up, however, is required to be effected in steps. The desired temperature can be either set manually or can be programmable for an interface integrated into a network portion.

According to the invention, the silicate sample, without prior purification, i.e. for example by desorption of water or OH— groups, can be decomposed in the graphite crucible 1, by the induction heating. In this manner the graphite crucible 1 is heated which results in a simultaneous heating up of the silicate sample. The temperature can be increased only slowly via the manual or programmable heating control. At a temperature of about 100 to 120° C., water can be desorbed and can be drawn off by the pump. With further temperature increase, other impurities can be fractionatingly vaporized. Thus at a temperature of about 1000° C. all OH— groups adherent to the sample are removed. Further, nitrogen groups which can quantitatively affect and falsify the latter analysis because of the molecular weight of $N_2$, can be driven off. At temperatures of about 1300 to 1400° C., the impurities are quantitatively removed and a further increase in the temperature results successively in a splitting off of the silicate oxygen which reacts with the graphite of the graphite crucible 1 to CO.

The heating can be carried out problem-free up to a temperature of 2200° C. In these experimental conditions, there is a Bouduard equilibrium between CO and $CO_2$ which lies entirely to the CO side. The presence of CO, as contrasted with $CO_2$, has the advantage that the CO as the substance to be analyzed has up to twice as great a sensitivity with respect to mass spectrometry than $CO_2$. Furthermore, the experiment with CO is shorter so that processing time is saved.

Thus, preferably the inductive heating is effective to the higher temperature at which the Bouduard equilibrium lies on the side of the CO. Alternatively, the CO produced by reaction of the oxygen with graphite can be transformed by a temperature lowering in the graphite crucible 1 to $CO_2$ based upon the Bouduard equilibrium when the equilibrium lies on the $CO_2$ side, the $CO_2$ can condense out in the cold finger 7. As a general matter in routine operations above all, the $CO_2$ is carried off in the helium carrier gas stream which is supplied by the helium on the feed line 13 through the connecting part or outlet 6 to the mass spectrometer. Based upon the different atomic weight of the two oxygen isotopes, the Co which is produced has a molecular weight of 28 or 30 in equilibrium with $CO_2$ with a molecular weight of 44 or 46. Thus it can also be advantageous to operate at a temperature which lies on the $CO_2$ side since its molecular weight cannot be confused with the $NO_2$ during the mass spectroscopic measurement in corresponding Faraday capture.

The method is usable for all oxygen-containing solids independently of whether they are available in powder form as amorphous masses, as crystals or some other solids form.

The possibility of continuously heating up of the sample material replaces the prepurification of the substance from undesired foreign substances or molecules by fractionated desorption or decomposition. As a result, a falsification of the output ratio of the oxygen isotopes is largely precluded since, by contrast with a chemical treatment, no exchange of oxygen atoms of the solid sample with oxygen atoms from reagents can occur. With mixtures which have different decomposition temperatures or melting or vaporization temperatures, a sequential oxygen isotope determination of the different components of the mixture can be carried out.

In an alternative embodiment of the method of the invention, the sample to be analyzed or to be liberated of the investigated solid is mixed with graphite powder and this mixture is inductively heated. The mixture can optionally be pressed into a solid form.

The graphite crucible 1 used in the apparatus according to the invention can have bores 11a, 11b which provide a connection between the bore 3 for receiving the rod 4 for mounting the graphite crucible 1 in the housing 5 and the interior space of the housing 5. This is then of advantage when impurity particles have deposited in the bore 3 which can interfere with the analysis. Bores 11a, 11b permit a decomposition of these foreign particles because they facilitate discharge from the bore 3.

Basically the graphite crucible 1 can also have another geometry so that the configuration of the graphite crucible 1 is not limited to the configuration shown in FIG. 1. A circular cross section is however the best for the inductive coupling, crucible manipulation and crucible production.

The graphite should be of high purity for the analytical purposes so that no falsification of the analysis results by impurities therefrom can occur. Preferably spectral graphite is used which contains any addition of carbon or other components only in a concentration below 20 ppm with Si<2 ppm, Ca<1 ppm, B<1 ppm, Fe<0.5 ppm, Ti<0.5 ppm. Since the analysis step which follows decomposition and reaction with graphite is not limited to mass spectrometry, the purity used can deviate and have other minimum values.

The method of the invention can be used to decompose and analyze large solid quantities of for example 500 μg in one experiment. The results are thus representative and are not subject to errors resulting from heterogeneity of the sample since in the measurement the entire sample is evaluated. Time-consuming repetitive measurements can therefore be spared.

EXAMPLE

The decomposition of silicates or opal silicon, as may occur in the shells of certain organisms like diatoms, is of special interest. The isotope ratio of oxygen contained therein can provide an indication of the ambient temperature at the time of formation of these silicon compounds. A pretreatment of these materials has previously been necessary to remove adherent water molecules and included OH groups.

In the method used as an example, the pretreatment is carried out in a single operating step with the liberation of the oxygen and its conversion into CO or $CO_2$. The material to be investigated is entered into the graphite crucible and mounted in the housing 5 and functions as a high temperature cell. After evacuation of this high temperature cell to $p \approx 10^{-6}$ bar, a slow inductive heating up of the graphite crucible 1 is effected. As a result initial adsorbed water is desorbed and pumped off ($T \leq 120°$ C.). With increasing temperature the included OH groups are removed. Following the ending of this procedure the material is heated up to 2000 to 2200° C. at which the $SiO_2$ is decomposed and the oxygen reacted with the graphite of the graphite crucible 1 to $CO_2$ and/or CO. Based upon the Bouduard equilibrium at temperatures of about 2000°, practically only CO is present in the gas space. This can be entrained after the end of the heating step on line by means of helium as a carrier gas into the analyzer in the form of isotope mass spectrometer.

Alternatively, instead of CO, $CO_2$ can also be mass spectrometrically analyzed. For this purpose, after the end of the decomposition time the graphite crucible 1 is slowly cooled whereupon the Bouduard equilibrium is then shifted to the $CO_2$ side. After termination of the cooling step $CO_2$ can be entrained on line with the aid of helium as a carrier gas, analogously to the $CO_2$, on line, for determination of the oxygen isotope ratio measurements (flow mode).

We claim:

1. A method of analyzing an oxygen-containing solid to determine its isotope ratio of oxygen isotopes $O^{16}$ to $O^{18}$ in said oxygen-containing solid, which comprises the steps of:
   (a) contacting the oxygen-containing solid with graphite;
   (b) inductively heating up the oxygen-containing solid in contact with the graphite to a temperature sufficient to decompose the oxygen-containing solid thereby liberating oxygen from the oxygen-containing solid which reacts with the graphite to form CO and/or $CO_2$; and
   (c) analyzing the isotope ratio of $O^{16}$ to $O^{18}$ in the CO and/or $CO_2$ obtained according to step (b), and relating the isotope ratio of $O^{16}$ to $O^{18}$ in the oxygen-containing solid to the ambient temperature at the time of formation of said oxygen-containing solid.

2. The method defined in claim 1, wherein according to step (b) the heating up of the oxygen-containing solid is effected in vacuum.

3. The method defined in claim 1, following step (b), further comprising the step of isolating the CO and/or $CO_2$, resulting from the heating up of the oxygen-containing solid.

4. The method defined in claim 1, wherein according to step (c) the isotope ratio of $O^{16}$ to $O^{18}$ in the CO and/or $CO_2$ is analyzed using mass spectroscopy.

5. The method defined in claim 1, wherein according to step (a) the oxygen-containing solid is a silicate.

6. The method defined in claim 1, wherein according to step (a) the oxygen-containing solid is a silicate, and wherein according to step (b) the heating up of the silicate is carried out at a temperature of 1600 to 2200° C.

7. The method defined in claim 1, wherein according to step (b) the heating up of the oxygen-containing solid is carried out sequentially to drive off impurities.

* * * * *